United States Patent [19]

Jolson et al.

[11] Patent Number: 5,338,429
[45] Date of Patent: Aug. 16, 1994

[54] ELECTROCHEMICAL TOXIC GAS SENSOR

[75] Inventors: Joseph D. Jolson, Pittsburgh; Alan A. Schneider, Wexford, both of Pa.

[73] Assignee: Mine Safety Appliances Company, Pittsburgh, Pa.

[21] Appl. No.: 27,044

[22] Filed: Mar. 5, 1993

[51] Int. Cl.$^5$ .............................. G01N 27/26
[52] U.S. Cl. .................. 204/415; 204/431; 204/432; 204/412
[58] Field of Search ............... 204/415, 431, 432, 412

[56] References Cited

U.S. PATENT DOCUMENTS 4,025,412  5/1977  LaConti ........................ 204/432
4,707,242 11/1987  Schneider et al. ............. 204/432

Primary Examiner—John Niebling
Assistant Examiner—Bruce F. Bell
Attorney, Agent, or Firm—James G. Uber

[57] ABSTRACT

A compact electrochemical gas sensor for detecting toxic gases is described which utilizes a fluted electrically-conducting feedthrough for making the electrical connection from outside the sensor with each electrode inside the sensor. Utilization of the fluted electrically-conducting feedthroughs significantly reduces the number of parts needed to make the sensor as well as reduces the likelihood of electrolyte leakage from the sensor. Additionally, the electrochemical toxic gas sensor may use a gas permeable membrane instead of a gas porous membrane.

20 Claims, 4 Drawing Sheets

ELECTROCHEMICAL TOXIC GAS SENSOR

FIELD OF THE INVENTION

The present invention relates to electrochemical gas sensors that are used for the detection of a variety of toxic gases such as carbon monoxide, chlorine, hydrogen cyanide, hydrogen sulfide, nitrogen dioxide and sulfur dioxide.

BACKGROUND OF THE INVENTION

In a typical electrochemical gas sensor, the gas to be measured diffuses from the atmosphere through a gas porous membrane to a working electrode where a chemical reaction occurs. The type, rate, and efficiency of the chemical reaction is controlled by the material used to make the working electrode, the diffusion rate of the gas to the working electrode, and the potential at which the working electrode is set in relation to a reference, another electrode. The working electrode potential is commonly set with the aid of a potentiostat circuit, but this is not necessarily a required operating mode. At the counter electrode, a chemical reaction complementary to the one occurring at the working electrode takes place. The current flow between the working electrode and the counter electrode is proportional to the concentration of the gas being measured. An ionically conductive liquid electrolyte contacts all the electrodes and allows charge balance to be maintained within the sensor. Such electrochemical gas sensors are generally disclosed and described in U.S. Pat. Nos. 4,132,616; 4,324,632; 4,474,648; and in European Patent Application No. 0 496 527 A1.

An exploded view of a presently-known electrochemical gas sensor used for detecting carbon monoxide is shown in FIG. 1. During assembly of such a sensor, a platinum counter electrode 2 is placed on the inside bottom of a sensor housing 4. The counter electrode 2 typically includes a gas porous membrane 3 such as Gortex® or Zitex®. Next, a gold-coated current collector 6 is placed in the sensor housing 4 in a manner allowing the gold-plated ring to contact the perimeter of the counter electrode 2 and the tab to extend through a lower hole (not shown) in the sensor housing 4 on top of the current collector 6. An O-ring 8 is then placed in the sensor housing 4 with the main spacer 10 being placed on top of the O-ring 8.

With these pieces in place, an electrically insulating but porous separator 12 is placed within the main spacer 10 and then a wick 14 is placed over the separator 12. Preferably, the wick is dumbbell-shaped and made from porous polyethylene or polypropylene which has been treated to make it hydrophilic. A second O-ring 16 is then placed over the main spacer 10 and a second gold-coated current collector 18 is placed on top of this O-ring 16 with the tab extending through a middle hole (not shown) in the sensor housing 4. Next, a platinum reference electrode 20 which has a center hole 22 is placed over the current collector 18 in a manner allowing them to make electrical contact. A third O-ring 24 is then placed over the reference electrode followed by a spacer 26 and one or more separators 28. Separators 28 are similar to separator 12.

A third gold-coated current collector 30 is then placed over this assembly with its tab extending through an upper hole (not shown) in the sensor housing 4. A platinum working electrode 32 is placed over the current collector 30. The working electrode 32 is similar in structure to the counter electrode 2 and also includes a gas porous membrane such as Gortex® or Zitex®. The working electrode 32 is inserted face down whereas the counter electrode is face up.

The sensor inlet assembly 34 which includes a baffle 36 to reduce convection is then pushed down over the stack and forms the top of sensor housing 4. The entire structure is maintained under some pressure in sensor housing 4 by fitting a retaining ring 38 into a groove 40 at the top of the sensor housing 4. Later, the tabs of the current collectors which extend through the lower, middle and upper holes are bent parallel to, and heat sealed to, the outer wall of the sensor housing 4. The area around where the tabs protrude through the holes in the sensor housing 4 is then coated with a hydrophobic sealant. After this sealant has dried, the sensor is filled with an ionically conductive aqueous sulfuric acid electrolyte through a fill hole 42 near the bottom of the sensor housing 4 which is then sealed with plug 44.

Toxic gas sensors utilizing this configuration have several disadvantages. Among them are high manufacturing costs which are due to the numerous parts used in the sensor as well as the labor involved with assembling the sensor and with applying the heat seal and hydrophobic sealants. Additionally, the high cost of precious metals such as the gold in the current collectors requires the use of fragile, laminated leads which are not very sturdy and which must be protected from mechanical abuse while still allowing for reliable external electrical connections. Even with the use of gaskets or O-rings, and hydrophobic sealants, sensors of this type still tend to leak electrolyte after long periods of use or after exposure to elevated temperatures. The leakage of the liquid electrolyte, typically aqueous sulfuric acid, not only reduces the performance characteristics of the sensor but can also corrode and destroy the instrument in which the sensor is located. Still another drawback to this type of sensor is its size which is over one inch in height.

Toxic gas sensors such as the one shown in FIG. 1 and described above do not use gas permeable membranes because the permeability of well known materials to gases and vapors is either too low or the materials are not sufficiently inert to withstand typical toxic gas sensing environments. As a result, toxic gas sensors utilize gas porous membranes such as Gore-Tex® or Zitex®. These gas porous membranes are usually made out of PTFE (polytetrafluoroethylene) which contain a large number of microscopically visible holes which are on the order of several microns in diameter. These holes typically cover about 60–70% of the geometric area of the gas porous membrane.

Although electrochemical toxic gas sensors made with gas porous membranes work acceptably in many applications, they are generally acknowledged to have several drawbacks. For example, the porosity of a gas porous membrane, for the most part, limits the choice of acceptable liquid electrolytes which can be used in the sensor primarily to aqueous acids. Even when using such aqueous acids, application of a pressure differential to the sensor can cause the electrolyte to weep through the porous membrane.

Additionally, water vapor rapidly transpires through a gas porous membrane as temperature and humidity change. This makes it necessary to leave space in the body of the sensor for a relatively large electrolyte reservoir. This increases the complexity of the sensor and causes the sensor to be larger than desirable. It also causes the pH of the electrolyte to change which changes the potential of the reference electrode in the sensor. The drift in the potential of the reference electrode results in zero drift, span drift and temperature compensation problems when using the sensor in an instrument. Also, aerosols, particles, and high molecular weight gases can easily pass through the microscopic holes in a porous membrane, causing poisoning of the sensing electrode. This poisoning phenomena results in a slow decline in sensor output with time until the sensor is chemically destroyed and no longer useable.

It would be desirable, therefore, to have an electrochemical toxic gas sensor which did not have these drawbacks.

SUMMARY OF THE INVENTION

Generally, the present invention relates to an electrochemical gas sensor comprising: a housing; a working electrode, a counter electrode, and a liquid electrolyte within the housing; a gas porous membrane for keeping the liquid electrolyte within the housing; and an electrical contact for each electrode which passes through the housing, the electrical contact comprising an electrically-conducting feedthrough having a flute. Preferably the present invention also has a reference electrode. If no separate reference electrode is used, the counter electrode also serves as the reference electrode.

Preferably a fluted non-precious metal pin is used as the feedthrough to make the necessary electrical contact from outside the sensor to each electrode within the sensor housing. This is especially the case if an aqueous acid electrolyte such as sulfuric acid is used in the sensor. Preferably, the sensor housing is made of a plastic material so that fluted non-precious metal pins can be insert-molded therein.

The toxic gas sensor of the present invention may also use a gas permeable membrane instead of a gas porous membrane as the primary boundary layer between the toxic gas to be sensed and the contents of the electrochemical gas sensor. A gas permeable membrane is one wherein the gas first dissolves in the material of the membrane before it can diffuse through the material since there are no holes in the membrane. This is different from the gas porous membrane described above wherein the gas diffuses directly through the microscopic holes in the membrane. The gas permeable membrane may be placed directly over a conventional working electrode which typically includes a gas porous membrane. In this configuration, the gas permeable membrane may be heat-sealed to the top of the sensor housing along with the gas porous membrane of the working electrode or it may be sealed to the housing along its perimeter by using other conventional means such as O-ring seals. In a preferred embodiment of the present invention, a second gas permeable membrane is used to seal the bottom of the sensor housing.

The electrocatalytic material such as platinum used to form the working electrode may be applied directly on or adjacent to the gas permeable membrane. If this method of fabrication is chosen, the gas porous membrane can be completely eliminated. Alternately, the gas permeable membrane can be heat-laminated directly to a gas porous membrane that has been coated with an electrode material on one face.

Other details, objects and advantages of the present invention will become apparent as the following description of the presently preferred embodiments of practicing the invention proceeds.

BRIEF DESCRIPTION OF THE DRAWINGS

In the accompanying drawings, preferred embodiments of the invention are illustrated in which.

DETAILED DESCRIPTION OF THE INVENTION

Figure 2:
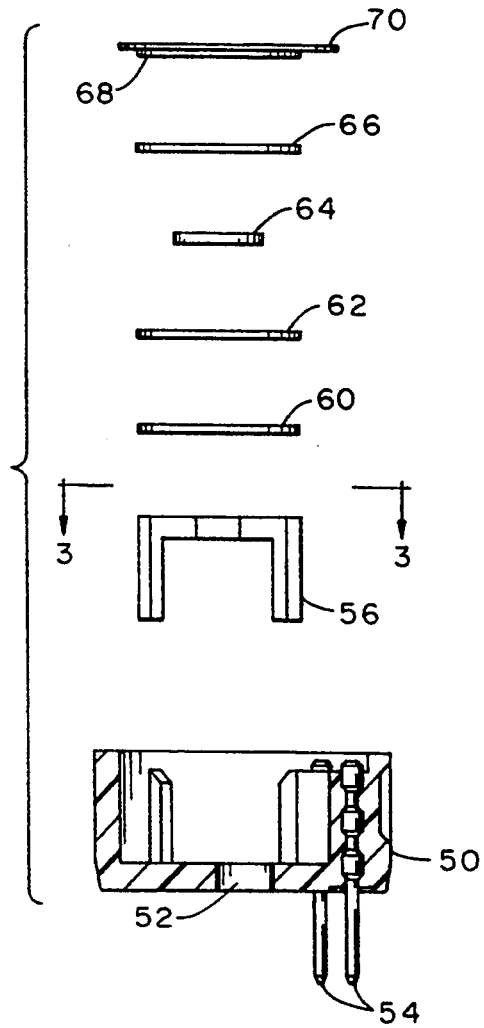
FIG. 2 is an exploded view of one embodiment of an electrochemical toxic gas sensor of the present invention.
Figure 3:
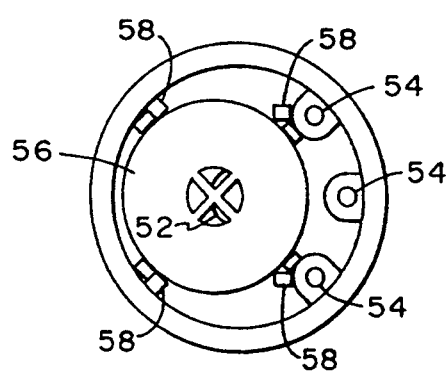
FIG. 3 is a top view of the sensor shown in FIG. 2 taken along line AA'.

A preferred embodiment of the electrochemical toxic gas sensor of the present invention is shown in FIG. 2 as it would be assembled to detect for carbon monoxide. The sensor has a housing 50 preferably made of a plastic material such as polyethylene with a small hole 52 in the bottom. The small hole 52 allows for the addition of the liquid electrolyte during assembly. The sensor also has a plurality of fluted titanium pins 54, which are preferably insert-molded into the plastic housing 50. These pins 54 are the electrically-conducting feedthroughs which allow for electrical contact between the electrodes inside the housing 50 and the outside of the sensor. Within the housing 50 is placed an electrode table or shelf 56. The table 56 is preferably made of a flexible plastic material similar to the housing 50 and is held in place by four tabs or posts 58 as shown in FIG. 3. The electrochemical components of the sensor are then stacked on the table 56. The space under the table 56 serves as a reservoir for the liquid electrolyte.

During assembly of the sensor, the electrode table 56 is inserted into the plastic housing 50. An electrically conducting and inert metal lead, such as short strips of platinum foil (not shown) having a thickness of about 3 mil, are spot-welded to the top of the titanium pins 54 and then bent upright. A counter electrode 60 is placed face up on the electrode table 56 and a first appropriate platinum foil lead is bent back over the counter electrode 60 allowing for good electrical contact. A separator 62 is then placed over this assembly. Next, a platinum reference electrode 64 is placed over the separator 62 and a second appropriate platinum foil lead is bent back contacting this electrode. A second separator 66 is then placed over this assembly. This separator 66 preferably has tabs which extend below the level of the electrode table 56 to allow liquid electrolyte from the reservoir to wick in to the electrochemical components and ionically connect all the electrodes with the sensor placed in any orientation.

Next, the remaining platinum foil lead is bent back over the second separator 66. The platinum working electrode 68 is typically located on the under side of a gas porous membrane 70 which is then placed over this assembly so that the gas porous membrane 70 is exposed to the atmosphere and the working electrode 68 contacts the foil lead. The gas porous membrane 70 is then heat-sealed to the top of the plastic housing 50. The housing 50 is then turned upside down and partially filled through small hole 52 with a liquid electrolyte such as aqueous sulfuric acid. Preferably a piece of gas porous material is placed over the small hole 52 and is heat-sealed to the housing 50. The electrodes and the separators described above are similar to those described in connection with FIG. 1.

The sensor of the present invention can then be placed within an outer housing (not shown) which is used to improve the electrical contact of the foil leads to the electrodes by compressing the electrochemical components, minimize air flow sensitivity, control temperature compensation requirements, improve signal linearity and uniformity, and adjust output sensitivity. The outer housing is not unlike the housing 4 and inlet assembly 34 shown in FIG. 1, but is smaller. Preferably the hole or holes in the outer housing above the working electrode are covered with a second gas porous membrane to prevent liquid transport into the sensor. The sensor remains open to the transpiration of water vapor and gases due to the gas porous membranes used therein.

Figure 4:
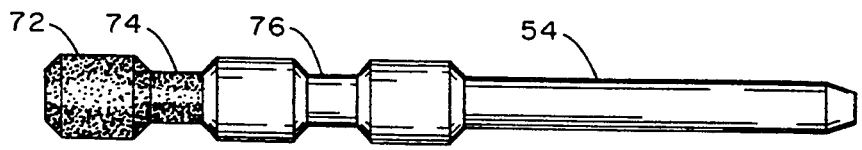
FIG. 4 is a preferred embodiment of the fluted electrically-conducted feedthrough used in the electrochemical toxic gas sensor of the present invention.

It was expected that over time the titanium pins 54 in the sensor would become covered with oxide and the liquid electrolyte would then wet the oxide layer and leak through it to the outside of the housing 50 because there is no chemical bond between the titanium pins 54 and the polyethylene housing 50. This is precisely what happens if non-fluted titanium pins are used. In practice, however, it has been found that there is no liquid electrolyte leakage in the gas sensor of the present invention. This is believed to be caused by the oxidation of the titanium surface in a flute of the electrically-conductive feedthrough. It appears that the creepage rate of the liquid electrolyte slows down or stops after an initial period of time if a fluted feedthrough such as a fluted titanium pin is used. A titanium oxide layer 72 appears to form on the upper end of the pin and stops increasing in length at the bottom of the neck of the first flute 74 as shown in FIG. 4. This phenomena can be observed under a microscope if the titanium pin 54 is removed from the polyethylene housing 50. What is observed is a titanium oxide layer starting at the top of the pin 54 which is exposed to the liquid electrolyte inside the housing. The titanium oxide layer continues to form within the polyethylene housing 50 as the pin narrows down into the first flute 74. It is believed that the growth of the oxide layer increases the effective diameter of the pin 54. The forces exerted by the increased pin diameter at the bottom of the neck of the first flute apparently push the pin 54 against the polyethylene housing 50 sufficiently hard to retard any further migration of liquid electrolyte past the bottom of the neck of the first flute 74 under normal sensor use conditions. No oxide layer is observed in the second flute 76 or on the surface of the pin 54 in the area between the flutes 74 and 76.

Sensors of the present invention are easy to assemble and have a much lower cost compared to presently known sensors. This is due in part to the reduction in the number of parts required for the sensor, i.e., no O-ring seals, gaskets, or hydrophobic sealants, as well as the reduced labor in assembling the sensor. It is also because the sensor requires less precious metal parts and simpler current collectors.

Figure 1:
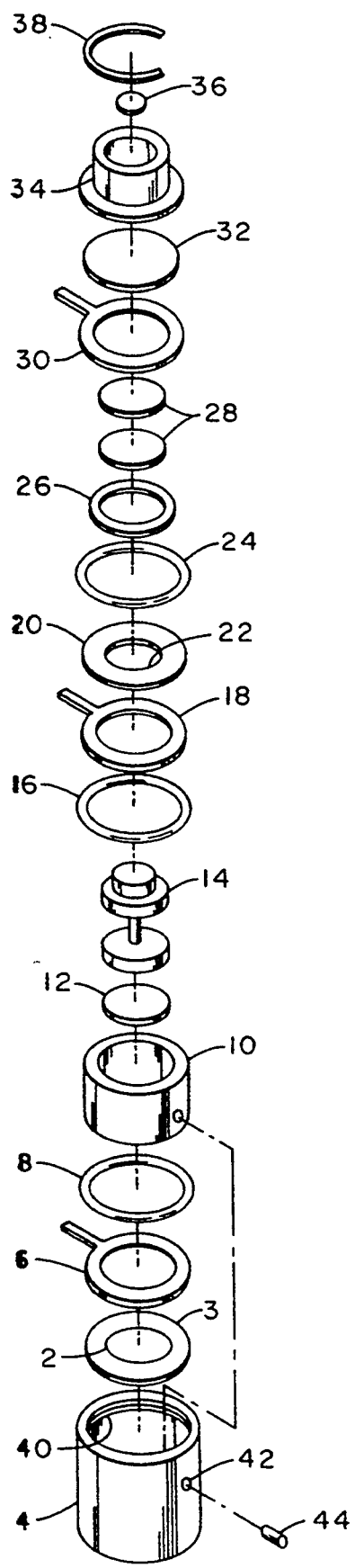
FIG. 1 is an exploded view of a presently known electrochemical toxic gas sensor for carbon monoxide.

The present invention also eliminates the leakage path which inevitably occurs through the O-ring seals in the sensor shown in FIG. 1. Sensors such as shown in FIG. 2 have been maintained at elevated temperatures of up to 60° C. for extended periods of time and have been temperature shocked repeatedly between 0° C. and 50° C. with no leakage of liquid electrolyte having been observed.

The sensor of the present invention is not limited to configurations having three electrodes but may be used in electrochemical sensors having two, four or more than four electrodes. Also, the sensor housing need not be polyethylene, although it should be insert-moldable and compatible with the liquid electrolyte chosen. Plastics which meet these requirements when aqueous acid electrolytes are used include fluoropolymers such as Teflon ®, Halar ®, and Tefzel ®. Other plastics which could be used include polypropylene, nylon, ABS (acrylonitrile-butadiene styrene), and polycarbonate.

Other materials which can be used for the electrically-conductive feedthroughs include those non-precious metals or metal alloys which form tenacious oxide films and therefore do not corrode at an appreciable rate in aqueous acid electrolytes. Such semi-noble metals include tantalum and zirconium in addition to titanium. Of course, the pins could be made from precious or noble metals such as gold, palladium, platinum and iridium since these materials are inert and do not form an oxide coating which will wick the liquid electrolyte out of the sensor housing at low potentials. However, at high enough oxidizing potentials, even noble metals will form a tenacious oxide coating in the same manner as semi-noble metals. Noble metal-plated semi-noble metal pins could also be used.

While only a single flute appears to be necessary, it is preferable to have more than one flute in the electrically-conducting feedthrough. Similarly, flutes of various shapes and sizes can be used in the sensor of the present invention. It is believed that a V-shaped or U-shaped flute, or any shape in between, will also work. The shape of the flutes shown in FIG. 4 was chosen for their ability to mechanically hold the pin in the housing after the pin was insert-molded into the housing.

Additional advantages are obtained if the sensor shown in FIG. 2 is also provided with a gas permeable membrane. Thin PTFE membranes, such as a ¼ mil PTFE film, have been found to provide sufficient gas permeability to allow the sensing of toxic gases. In one test, a ¼ mil PTFE film was placed over the porous membrane of the sensor shown in FIG. 2. An O-ring was placed over the film. An outer housing was then placed around the assembly compressing the O-ring and sealing the film to gas transport around the perimeter via the O-ring. The working electrode was then set to 0.00 volts using a low cost potentiostat. After ten minutes in air, the base current stabilized. Using flow meters to adjust the gas concentration to ±10% accuracy the sensor was then tested for response to carbon monoxide yielding the data shown in TABLE 1.

TABLE 1

| ppm CO (in air) | Sensor Output (μA) |
| --- | --- |
| 0 | −0.02 |
| 114 | 0.44 |
| 206 | 0.84 |
| 281 | 1.08 |
| 468 | 1.54 |
| 515 | 1.65 |
| 562 | 1.77 |
| 634 | 1.90 |
| 687 | 2.10 |
| 736 | 2.17 |
| 792 | 2.25 |

TABLE 1-continued

| ppm CO (in air) | Sensor Output (μA) |
| --- | --- |
| 858 | 2.45 |
| 883 | 2.50 |
| 951 | 2.70 |
| 1030 | 2.90 |

Figure 5:
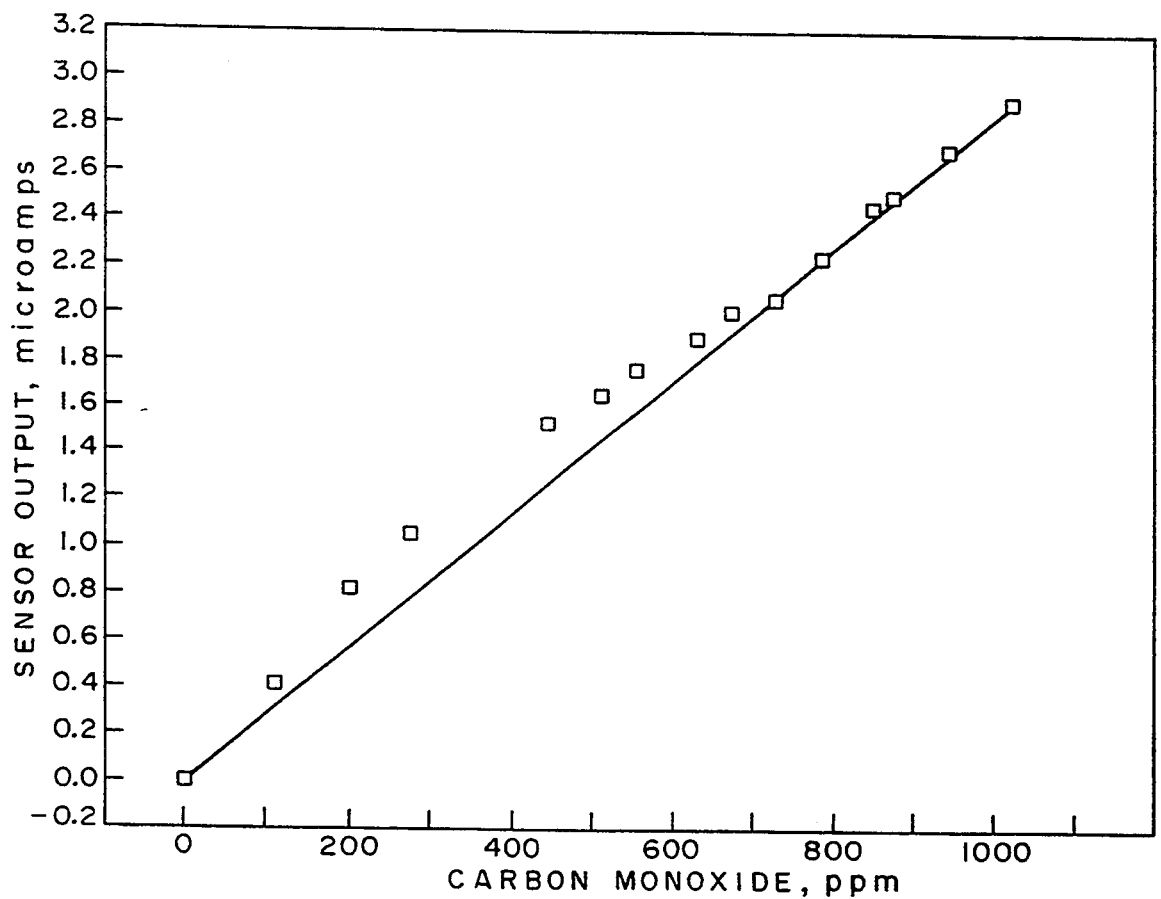
FIG. 5 is a graph of the data shown in TABLE 1.

When plotted such as is shown in FIG. 5, this data indicates that, within experimental error, the sensor was linear over the entire carbon monoxide concentration range studied. The electrical output of the sensor was approximately 2.8 nanoamps/ppm carbon monoxide.

In a second, more controlled set of experiments with the same sensor, a PAR Model #363 potentiostat was used to set the working electrode potential to 0.000 volts vs. the reference electrode. A Sierra mass flow gas proportioner with a ±2% accuracy was used to mix air and a tank of 5.14% carbon monoxide in air to various concentrations while maintaining a flow rate of 300 cc/min. The data shown in TABLE 2 was obtained:

TABLE 2

| ppm CO (in air) | Sensor Output (μA) |
| --- | --- |
| 0 | −0.01 |
| 0.17 | 5.0 |
| 0.34 | 9.2 |
| 0.69 | 18.3 |
| 1.37 | 36.4 |
| 2.06 | 54.6 |
| 2.74 | 73.3 |
| 3.43 | 90.8 |
| 4.11 | 109 |
| 4.45 | 122 |
| 4.80 | 132 |
| 4.97 | 136 |
| 5.14 | 142 |

Figure 6:
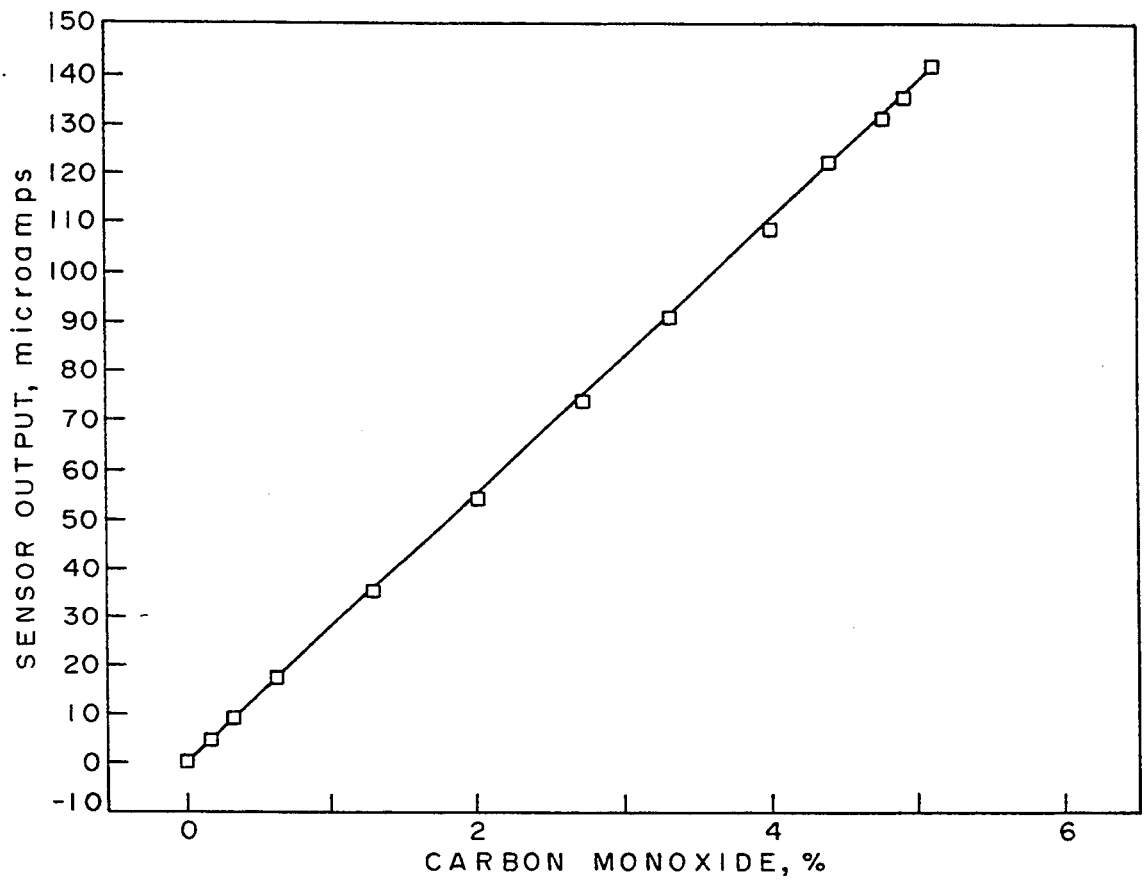
FIG. 6 is a graph of the data shown in TABLE 2.
Figure 7:
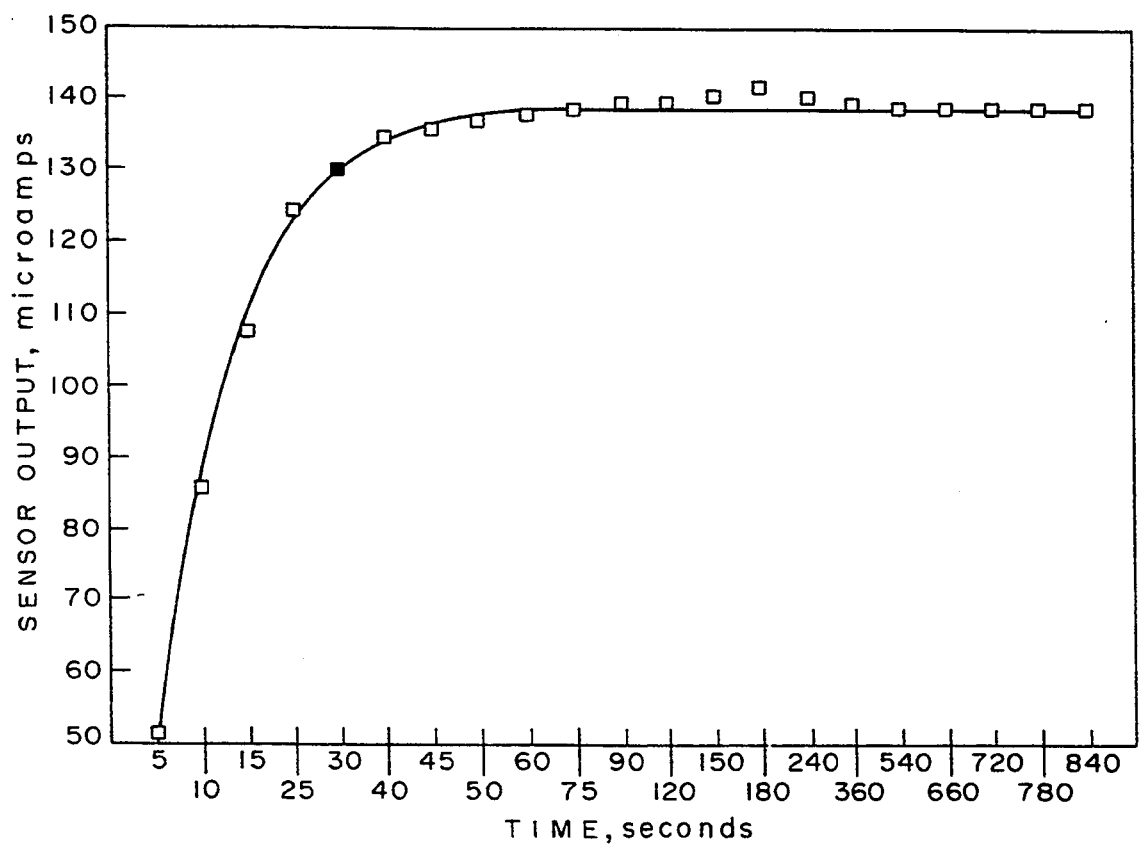
FIG. 7 is a graph of the data shown in TABLE 4.

When plotted such as shown in FIG. 6, it is found that the sensor was linear over the entire concentration range studied. The electrical output of the sensor was approximately 27 microamps/percent CO and agreed well with the results in TABLE 1.

The output of the sensor as a function of gas flow rate at 5.14% CO in air was then studied and the data in TABLE 3 was obtained:

TABLE 3

| Flow Rate (cc/min) | Sensor Output (μA) |
| --- | --- |
| 0 | — |
| 10 | 132 |
| 20 | 135 |
| 40 | 137 |
| 80 | 138 |
| 160 | 140 |
| 300 | 143 |

The electrical output of the sensor at a gas flow rate of zero declined slowly as the carbon monoxide was consumed. However, only an 8% change in electrical output was noted from 10 to 300 cc/min gas flow.

The response time of the sensor to 5.14% CO at 300 cc/min was then studied yielding the data shown in TABLE 4:

TABLE 4

| Time (sec) | Sensor Output (μA) |
| --- | --- |
| 0 | −0.1 |
| 5 | 52.0 |
| 10 | 86.2 |
| 15 | 107.8 |
| 25 | 124.5 |
| 30 | 130.0 |
| 40 | 134.5 |
| 45 | 135.7 |
| 50 | 136.6 |
| 60 | 137.6 |
| 75 | 138.7 |
| 90 | 139.4 |
| 120 | 139.4 |
| 150 | 140.2 |
| 180 | 141.6 |
| 240 | 140.2 |
| 360 | 139.2 |
| 540 | 138.8 |
| 660 | 138.8 |
| 720 | 138.8 |
| 780 | 138.9 |
| 840 | 138.8 |

When plotted such as shown in FIG. 6, a well defined curve is obtained with 90% of final output achieved in 25 seconds and 97% of final output achieved in 45 seconds.

Another sensor was fabricated which was similar to the above sensor except that the ¼ mil PTFE film (i.e., the gas permeable membrane) was heat-laminated to the membrane which was part of the working electrode. This process changed the crystallinity of the PTFE thereby reducing its permeability. Therefore, output of this sensor to carbon monoxide was only 0.75 nanoamps/ppm. This sensor was also exposed to 1,893 ppm $H_2S$ in $N_2$. A rapid response of 4.35 microamps or 2.3 nanoamps/ppm $H_2S$ was observed.

The ¼ mil PTFE film was supplied by CHEMFAB. This is not the only gas permeable film currently available with sufficient permeability and chemical stability to meet the requirements of electrochemical toxic gas sensors. For example, CHEMPLAST supplies a ½ mil PTFE material and Dupont supplies a ½ mil FEP Teflon ® material which should also work.

Materials having higher gas permeabilities would provide increased outputs. This would allow the potentiostat to be less complex and/or allow for lower gas detection limits. Materials with the chemical stability associated with fluoropolymers but with a much higher gas permeability than PTFE are currently available. Examples of such materials are Teflon ® AF-1600 and Teflon ® AF-2400 manufactured by Dupont. These materials are copolymers of perfluoro (2,2-dimethyl-1,3-dioxole) and tetrafluoroethylene. Teflon AF-1600 is available in 1, 2 and 10 mil films and has gas permeabilities approximately two orders of magnitude higher than PTFE. Silicone polymers can also be fluorinated resulting in a material which combines the high gas permeability of silicone polymers with the chemical inertness expected from fluorinated polymers.

Another material with gas permeability several orders of magnitude higher than that of PTFE while having adequate chemical inertness for use in some electrochemical gas sensing applications is a copolymer of silicone and polycarbonate. It is manufactured by Membrane Products Company and sold as MEM-213 in films between 1 and 10 mils in thickness. MEM-213 is also available in ultrathin films on microporous supports.

Comparable gas permeability data to toxic gases does not exist for the above mentioned gas permeable membranes. However, the relative gas permeability of these materials may be grasped by considering the data for oxygen which is provided below:

| Material | Oxygen Permeability (centi-barrer) |
| --- | --- |
| PTFE | 420 |
| MEM-213 | 16,000 |
| Teflon AF-1600 | 34,000 |
| Teflon AF-2400 | 99,000 |

Note that the permeability of Teflon ® AF-1600 and AF-2400 are high enough to allow outputs with thin films of this material to be comparable to those obtained with gas porous membranes.

Toxic gas sensors which have a gas permeable membrane between the electrochemically active portion of the device and the gas to be sensed are generally more robust and rugged than presently known sensors which use gas porous membranes. As a result of using a gas permeable membrane, the sensors will be more able to withstand environmental stresses such as, shock, bump, and vibration without leaking electrolyte. They will also be able to withstand and operate over a wider range of temperatures and pressures than sensors using only gas porous membranes.

The advantages of using a gas permeable membrane instead of a gas porous membrane will be fully realizable when using acidic, neutral, or alkaline aqueous electrolytes such as aqueous acetic acid, aqueous potassium chloride, or aqueous potassium hydroxide, respectively. Non-aqueous electrolytes, with organic as well as inorganic solvents, can also be used with gas permeable membranes. In contrast, only aqueous acidic electrolytes can be readily used with sensors having only gas porous membranes. When neutral aqueous or organic electrolytes are used with sensors having only gas porous membranes, the sensors experience a significant reduction in their ability to withstand environmental abuse. Successful use of aqueous alkaline or inorganic electrolytes has never been achieved with toxic gas sensors using only gas porous membranes.

When using aqueous electrolytes with sensors having only a gas permeable membrane, water vapor exchange rates with the atmosphere will be minimized. When using low vapor pressure non-aqueous electrolytes with minimal water solubility, water exchange will be virtually eliminated. This will stabilize the potential of the reference electrode allowing calibration frequencies to be significantly reduced and detection limits to be lowered.

Lower detection limits will also be achievable because the gas permeable membrane will control the temperature compensation requirements of the sensor. This is a significant improvement because the properties of the gas permeable film will remain constant with time. Accurate temperature compensation has been difficult to achieve using sensors having only gas porous membranes in part, because pH changes shift the reference electrode potential.

With the use of gas permeable membranes, poisoning of the sensing electrode will be minimized because aerosols, particles, and high molecular weight gases will not have direct access to the electrochemically active portion of the sensor. For example, the effects of salt spray in marine environments will be greatly diminished. This will reduce the calibration frequency as well as increase the useful life of the sensor. It will also allow for use of less electrocatalyst when making the working electrode and the counter electrode. This will further reduce costs and could lead to a reduction in noise levels.

Sensors having a gas permeable membrane are expected to be less expensive to construct because the complex separator configurations required for wicking the liquid electrolyte to ensure omni-positional use may no longer be necessary. Also, since water exchange will be minimized, the size of the cavity or reservoir that must be set aside for the liquid electrolyte can be reduced and perhaps eliminated. This will allow for the design of significantly smaller electrochemical toxic gas sensors than was previously possible.

While presently preferred embodiments of the invention have been shown and described with particularity in connection with the accompanying drawings, the invention may be otherwise embodied within the scope of the following claims.

What is claimed is:

1. An electrochemical toxic gas sensor comprising a housing; a working electrode, a counter electrode, and a liquid electrolyte within the housing; the electrodes being electrically separate from one another but ionically connected via the electrolyte; a gas porous membrane for keeping the liquid electrolyte within the housing; and an electrical contact for each electrode which passes through the housing, the electrical contact comprising an electrically-conducting feedthrough having a flute.

2. The electrochemical sensor of claim 1 wherein the electrically-conducting feedthrough comprises a fluted pin made of a noble metal.

3. The electrochemical sensor of claim 1 wherein the electrically-conducting feedthrough comprises a fluted pin made of a semi-noble metal.

4. The electrochemical sensor of claim 3 wherein the fluted pin is made from the group of metals consisting of titanium, tantalum, zirconium, and any alloy thereof and mixture containing one or more of these metals.

5. The electrochemical sensor of claim 1 further comprising a gas permeable membrane for keeping the liquid electrolyte within the housing.

6. The electrochemical sensor of claim 1 further comprising a reference electrode placed between the working electrode and the counter electrode.

7. The electrochemical sensor of claim 6 wherein the electrically-conducting feedthrough comprises a fluted pin made of a noble metal.

8. The electrochemical sensor of claim 6 wherein the electrically-conducting feedthrough comprises a fluted pin made of a semi-noble metal.

9. The electrochemical sensor of claim 8 wherein the fluted pin is made from the group of metals consisting of titanium, tantalum, zirconium, and any alloy thereof and mixture containing one or more of these metals.

10. An electrochemical toxic gas sensor comprising a housing; a working electrode, a counter electrode, and a liquid electrolyte within the housing; the electrodes being electrically separate from one another but ionically connected via the electrolyte; an electrical contact for each electrode which passes through the housing; and a gas permeable membrane.

11. The electrochemical sensor of claim 10 wherein the gas permeable membrane comprises a thin film of a copolymer of perfluoro (2,2-dimethyl -1,3-dioxole) and tetrafluoroethylene.

12. The electrochemical sensor of claim 10 wherein the gas permeable membrane comprises a thin film of polyethylene, or polytetrafluoroethylene or fluorinated ethylene propylene copolymer.

13. The electrochemical sensor of claim 10 wherein the gas permeable membrane comprises a thin film of a fluorinated silicone polymer.

14. The electrochemical sensor of claim 10 wherein the gas permeable membrane comprises a thin film of a copolymer of silicone and polycarbonate.

15. The electrochemical sensor of claim 10 wherein the working electrode includes a gas porous membrane, the gas permeable membrane being positioned such that the toxic gas must first pass through the gas permeable membrane before reaching the working electrode.

16. The electrochemical sensor of claim 15 wherein the working electrode is placed adjacent to the gas permeable membrane.

17. The electrochemical sensor of claim 10 wherein the working electrode is fabricated on the inner surface of the gas permeable membrane.

18. The electrochemical sensor of claim 10 wherein the liquid electrolyte is selected from the group consisting of an aqueous acid electrolyte, an aqueous neutral electrolyte and an aqueous alkaline electrolyte.

19. The electrochemical sensor of claim 10 wherein the electrolyte comprises a non-aqueous organic solvent and a salt.

20. The electrochemical sensor of claim 10 wherein the electrolyte comprises a non-aqueous inorganic acid.

* * * * *